(12) United States Patent
Li et al.

(10) Patent No.: US 10,144,936 B2
(45) Date of Patent: Dec. 4, 2018

(54) METHOD OF ASSEMBLING MULTI-FRAGMENT DNA MOLECULE AND USE THEREOF

(71) Applicant: WUHAN BIORUN BIOTECHNOLOGY LIMITED LIABILITY COMPANY, Wuhan (CN)

(72) Inventors: Yang Li, Wuhan (CN); Yangsheng Li, Wuhan (CN)

(73) Assignee: WUHAN BIORUN BIOTECHNOLOGY LIMITED LIABILITY COMPANY, Wuhan (CN)

(*) Notice: Subject to any disclaimer, the term of this patent is extended or adjusted under 35 U.S.C. 154(b) by 25 days.

(21) Appl. No.: 14/862,133

(22) Filed: Sep. 22, 2015

(65) Prior Publication Data

US 2016/0083736 A1 Mar. 24, 2016

Related U.S. Application Data

(63) Continuation-in-part of application No. PCT/CN2014/072894, filed on Mar. 5, 2014.

(30) Foreign Application Priority Data

Mar. 22, 2013 (CN) .......................... 2013 1 0094572

(51) Int. Cl.
*C12N 15/64* (2006.01)
*C12N 15/66* (2006.01)
*C12N 15/63* (2006.01)
*C12P 19/34* (2006.01)

(52) U.S. Cl.
CPC ............. *C12N 15/64* (2013.01); *C12N 15/63* (2013.01); *C12N 15/66* (2013.01); *C12P 19/34* (2013.01)

(58) Field of Classification Search
None
See application file for complete search history.

(56) References Cited

U.S. PATENT DOCUMENTS 6,270,969 B1 * 8/2001 Hartley .................... C12N 9/00
435/320.1

OTHER PUBLICATIONS

Lin et al., Proc. Natl. Acad. Sci., 100(10): 5962-5967, 2003 (Year: 2003).*

* cited by examiner

*Primary Examiner* — Nancy A Treptow
(74) *Attorney, Agent, or Firm* — Matthias Scholl P.C.; Matthias Scholl (57) ABSTRACT

A method of assembling multi-fragment DNA molecule, the method including: 1) constructing a vector system including an acceptor vector A1, a first donor vector B1, and a second donor vector B2, and each of the acceptor vector A1, the second donor vector B2, and the second donor vector B2 including a multiple cloning site; 2) introducing a first target sequence $L_m$ to the first donor vector B1, m being an odd number starting from 1, and introducing a second target sequence $L_n$ to the second donor vector B2, n being an even number starting from 2; and 3) repeating 2) to assemble multiple fragments to yield a multi-fragment DNA molecule.

5 Claims, 1 Drawing Sheet

Specification includes a Sequence Listing.

FIG. 1 tagacgagacgagactgtcgtctcagtcg (SEQ ID NO: 4)

FIG. 2 cgtctc AGAGACCNN···NNGGTCTCN gaagagcaNN···NNGctctcggtcgcGagacg (SEQ ID NO: 5)

FIG. 3

GctctcNGAGACCNN···NNGGTCTCNGagacgNN···NNcgtctcggtcggaagagc (SEQ ID NO: 6)

SEQUENCE LISTING

<160> NUMBER OF SEQ ID NOS: 6

<210> SEQ ID NO 1
<211> LENGTH: 4147
<212> TYPE: DNA
<213> ORGANISM: Artificial Sequence
<220> FEATURE:
<223> OTHER INFORMATION: Fully synthetic

<400> SEQUENCE: 1

| | | | | | |
|---|---|---|---|---|---|
| cctaggccac | catggacaag | aagtactcca | ttgggctcga | tatcggcaca | aacagcgtcg | 60 |
| gctgggccgt | cattacggac | gagtacaagg | tgccgagcaa | aaaattcaaa | gttctgggca | 120 |
| ataccgatcg | ccacagcata | aagaagaacc | tcattggcgc | cctcctgttc | gactccgggg | 180 |
| aaacggccga | agccacgcgg | ctcaaaagaa | cagcacggcg | cagatatacc | cgcagaagaa | 240 |
| tcggatctgc | tacctccagg | agatctttag | taatgagatg | gctaaggtgg | atgactcttt | 300 |
| cttccatagg | ctggaggagt | cctttttggt | ggaggaggat | aaaaagcacg | agcgccaccc | 360 |
| aatctttggc | aatatcgtgg | acgaggtggc | gtaccatgaa | agtacccaa | ccatatatca | 420 |
| tctgaggaag | aagctggtag | acagtactga | taaggctgac | ttgcggttga | tctatctcgc | 480 |
| gctggcgcac | atgatcaaat | tcggggaca | cttcctcatc | gagggggacc | tgaacccaga | 540 |
| caacagcgat | gtggacaaac | tctttatcca | actggttcag | acttacaatc | agcttttcga | 600 |
| agagaaaccg | atcaacgcat | ccggagttga | cgccaaagca | atcctgagcg | ctaggctgtc | 660 |
| caaatcccgg | cggctcgaaa | acctcatcgc | acagctccct | ggggagaaga | gaacggcct | 720 |
| gtttggtaat | cttatcgccc | tgtcactcgg | gctgacccc | aactttaaat | ctaacttcga | 780 |
| cctgccgaa | gatgccaagc | tgcaactgag | caaagacacc | tacgatgatg | atctcgacaa | 840 |
| tctgctggcc | cagatcggcg | accagtacgc | agaccttttt | ttggcggcaa | agaacctgtc | 900 |
| agacgccatt | ctgctgagtg | atattctgcg | agtgaacacg | gagatcacca | agctccgct | 960 |
| gagcgctagt | atgatcaagc | gctatgatga | gcaccaccaa | gacttgactt | tgctgaaggc | 1020 |
| ccttgtcaga | cagcaactgc | tgagaagta | caaggaaatt | ttcttcgatc | agtctaaaaa | 1080 |
| tggctacgcc | ggatacattg | acggcggagc | aagccaggag | gaattttaca | aatttattaa | 1140 |
| gcccatcttg | gaaaaaatgg | acggcaccga | ggagctgctg | gtaaagctga | acagagaaga | 1200 |
| tctgttgcgc | aaacagcgca | ctttcgacaa | tggaagcatc | ccccaccaga | ttcacctggg | 1260 |
| cgaactgcac | gctatcctca | ggcggcaaga | ggatttctac | cctttttga | aagataacag | 1320 |
| ggaaaagatt | gagaaaatcc | tcacatttcg | gatacctac | tatgtaggcc | ccctcgcacg | 1380 |
| cggaaattcc | agattcgcgt | ggatgactcg | caaatcagaa | gaaccatca | ctccctggaa | 1440 |
| cttcgaggaa | gtcgtggata | agggggcctc | tgcccagtcc | ttcatcgaaa | ggatgactaa | 1500 |
| ctttgataaa | aatctgccta | acgaaaaggt | gcttcctaaa | cactctctgc | tgtacgagta | 1560 |
| cttcacagtt | tataacgaac | tcaccaaggt | caaatacgtc | acagaaggga | tgagaaagcc | 1620 |
| agcattcctg | tctggagagc | agaagaaagc | tatcgtggac | ctcctcttca | agacgaaccg | 1680 |
| gaaagttacc | gtgaaacagc | tcaaagagga | ctatttcaaa | aagattgaat | gtttcgactc | 1740 |
| tgttgaaatc | agcggagtgg | aggatcgctt | caacgcatcc | ctgggaacgt | atcacgatct | 1800 |
| cctgaaaatc | attaaagaca | aggacttcct | ggacaatgag | gaacgagg | acattcttga | 1860 |
| ggacattgtc | ctcaccctta | cgttgtttga | agatagggag | atgattgaag | aacgcttgaa | 1920 |
| aacttacgct | catctcttcg | acgacaaagt | catgaaacag | ctcaagaggc | gccgatatac | 1980 |
| aggatggggg | cggctgtcaa | gaaaactgat | caatgggatt | cgagacaagc | agagtggaaa | 2040 |

```
gacaatcctg gattttctta agtccgatgg atttgccaac cggaacttca tgcagttgat    2100
ccatgatgac tctctcacct ttaaggagga catccgaaaa gcacaagttt ctggccaggg    2160
ggacagtctg cacgagcaca tcgctaatct tgcaggtagc ccagctatca aaagggaat    2220
actgcagacc gttaaggtcg tggatgaact cgtcaaagta atgggaaggc ataagcccga    2280
gaatatcgtt atcgagatgg cccgagagaa ccaaactacc cagaagggac agaagaacag    2340
tagggaaagg atgaagagga ttgaagaggg tataaaagaa ctggggtccc aaatccttaa    2400
ggaacaccca gttgaaaaca cccagcttca gaatgagaag ctctacctgt actacctgca    2460
gaacggcagg acatgtacg tggatcagga actggacatc aatcggctct ccgactacga     2520
cgtggatcat atcgtgcccc agtctttct caaagatgat tctattgata taaagtgtt     2580
gacaagatcc gataaaaata gagggaagag tgataacgtc ccctcagaag aagttgtcaa    2640
gaaaatgaaa aattattggc ggcagctgct gaacgccaaa ctgatcacac aacggaagtt    2700
cgataatctg actaaggctg aacgaggtgg cctgtctgag ttggataaag ccggcttcat    2760
caaaaggcag cttgttgaga cacgccagat caccaagcac gtggcccaaa ttctcgattc    2820
acgcatgaac accaagtacg atgaaaatga caaactgatt cgagaggtga agttattac    2880
tctgaagtct aagctggtgt cagatttcag aaaggacttt cagttttata aggtgagaga    2940
gatcaacaat taccaccatg cgcatgatgc ctacctgaat gcagtggtag gcactgcact    3000
tatcaaaaaa tatcccaagc tggaatctga atttgtttac ggagactata agtgtacga    3060
tgttaggaaa atgatcgcaa agtctgagca ggaaataggc aaggccaccg ctaagtactt    3120
cttttacagc aatattatga attttttcaa gaccgagatt acactggcca atggagagat    3180
tcggaagcga ccacttatcg aaacaaacgg agaaacagga gaaatcgtgt gggacaaggg    3240
tagggatttc gcgacagtcc ggaaggtcct gtccatgccg caggtgaaca tcgttaaaaa    3300
gaccgaagta cagaccggag gcttctccaa ggaaagtatc ctcccgaaaa ggaacagcga    3360
caagctgatc gcacgcaaaa aagattggga ccccaagaaa tacggcggat tcgattctcc    3420
tacagtcgct tacagtgtac tggttgtggc caaagtggag aaaggaagt ctaaaaaact     3480
caaaagcgtc aaggaactgc tgggcatcac aatcatggag cgatcaagtt tcgaaaaaaa    3540
ccccatcgac tttctggagg cgaaaggata taagaggtc aaaaagacc tcatcattaa      3600
gctgcccaag tactctctct tgagcttga aacggccgg aaacgaatgc tcgctagtgc      3660
gggcgagctg cagaaaggta acgagctggc actgccctct aaatacgtta atttcttgta    3720
tctggccagc cactatgaaa agctcaaagg gtccccgaa gataatgagc agaagcagct     3780
gttcgtggaa caacacaaac actaccttga tgagatcatc gagcaaataa gcgagttctc    3840
caaaagagtg atcctcgccg acgctaacct cgataaggtg cttctgctt acaataagca    3900
cagggataag cccatcaggg agcaggcaga aaacattatc cacttgttta ctctgaccaa    3960
cttgggcgca cctgcagcct tcaagtactt cgacaccacc atagacagaa agcggtacac    4020
ctctacaaag gaggtcctgg acgccacact gattcatcag tcaattacgg ggctctatga    4080
aacaagaatc gacctctctc agctcggtgg agacagcagg gctgacccca agaagaagag    4140
gaaggtg                                                              4147

<210> SEQ ID NO 2
<211> LENGTH: 39
<212> TYPE: DNA
<213> ORGANISM: Artificial Sequence
<220> FEATURE:
```

<223> OTHER INFORMATION: Fully synthetic

<400> SEQUENCE: 2
ggtctcatct catagacatg gagtcaaaga ttcaaatag                    39

<210> SEQ ID NO 3
<211> LENGTH: 38
<212> TYPE: DNA
<213> ORGANISM: Artificial Sequence
<220> FEATURE:
<223> OTHER INFORMATION: Fully synthetic

<400> SEQUENCE: 3
ggtctctctt ctctagtttt tttttaggc catccgct                     38

<210> SEQ ID NO 4
<211> LENGTH: 30
<212> TYPE: DNA
<213> ORGANISM: Artificial Sequence
<220> FEATURE:
<223> OTHER INFORMATION: Fully synthetic

<400> SEQUENCE: 4
tagacgagac gagactgtcc gtctcagtcg                             30

<210> SEQ ID NO 5
<211> LENGTH: 52
<212> TYPE: DNA
<213> ORGANISM: Artificial Sequence
<220> FEATURE:
<223> OTHER INFORMATION: Fully synthetic
<220> FEATURE:
<221> NAME/KEY: Unsure
<222> LOCATION: (14)..(18)
<220> FEATURE:
<221> NAME/KEY: misc_feature
<222> LOCATION: (14)..(18)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t

<400> SEQUENCE: 5
cgtctcagag accnnnnngg tctcngaaga gcagctcttc ggtcgcgaga cg    52

<210> SEQ ID NO 6
<211> LENGTH: 55
<212> TYPE: DNA
<213> ORGANISM: Artificial Sequence
<220> FEATURE:
<223> OTHER INFORMATION: Fully synthetic
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: Unsure
<222> LOCATION: (15)..(18)
<220> FEATURE:
<221> NAME/KEY: misc_feature
<222> LOCATION: (15)..(18)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: Unsure
<222> LOCATION: (32)..(37)
<220> FEATURE:

```
<221> NAME/KEY: misc_feature
<222> LOCATION: (32)..(37)
<223> OTHER INFORMATION: n is a, c, g, or t

<400> SEQUENCE: 6
gctcttcnga gaccnnnngg tctcngagac gnnnnnncgt ctcggtcgga agagc          55
```

METHOD OF ASSEMBLING MULTI-FRAGMENT DNA MOLECULE AND USE THEREOF

CROSS-REFERENCE TO RELATED APPLICATIONS

This application is a continuation-in-part of International Patent Application No. PCT/CN2014/072894 with an international filing date of Mar. 5, 2014, designating the United States, now pending, and further claims priority benefits to Chinese Patent Application No. 201310094572.6 filed Mar. 22, 2013. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, Mass. 02142.

BACKGROUND OF THE INVENTION

Field of the Invention

The invention relates to a method of assembling multi-fragment DNA molecule and use thereof.

Description of the Related Art

Typically, a DNA polymerase is able to amplify a DNA sequence to be no more than 10 kb, and the amplified DNA sequence has high mutation rate and requires sequencing and reverse mutation, which is time and labor consuming. The synthesis of a complete gene having long DNA sequences requires multiple cycles of PCR and specific splicing, which also involves multiple mutations. In addition, the construction of a multiple gene vector is complicate, the introduction of each single gene is a multi-step process, and the introduced genes are spliced at intervals.

SUMMARY OF THE INVENTION

In view of the above-described problems, it is one objective of the invention to provide a method of assembling multi-fragment DNA molecule and use thereof. The method is adapted to seamlessly assemble multiple DNA fragments into an integral large DNA fragment and the can be applied in gene fragment synthesis, construction of transgenic vector for multiple genes, and synthetic biology.

To achieve the above objective, in accordance with one embodiment of the invention, there is provided a method of assembling a multi-fragment DNA molecule. The method comprises:

1) constructing a vector system comprising an acceptor vector A1, a first donor vector B1, and a second donor vector B2, and each of the acceptor vector A1, the second donor vector B2, and the second donor vector B2 comprising a multiple cloning site;

where, the multiple cloning site of the acceptor vector A1 comprises one group of restriction sites of a restriction enzyme and has a sequence of "a vector backbone—a reverse restriction site of a restriction enzyme at an odd number site—arbitrary bases—a forward restriction site of the restriction enzyme at the odd number site—the vector backbone"; and the vector backbone is in the absence of any restriction site of the restriction enzyme;

the multiple cloning site of the first donor vector B1 comprises three groups of restriction sites of restriction enzymes and the first target sequence $L_m$ is added to a left side of the multiple cloning site; the sequence of the multiple cloning site of the first donor vector B1 is represented by "a vector backbone—the forward restriction site of the restriction enzyme at the odd number site—a reverse restriction site of a cloning restriction enzyme—arbitrary bases—a forward restriction site of the cloning restriction enzyme—a reverse restriction site of a restriction enzyme at an even number site—arbitrary bases—a forward restriction site of the restriction enzyme at the even number site—the reverse restriction site of the restriction enzyme at the odd number site—the vector backbone"; all restriction sites of the cloning restriction enzyme in the vector backbone of the first donor vector B1 are removed, and m represents an odd number, such as 1, 3, 5, 7, and so on; and the multiple cloning site of the second donor vector B2 comprises three groups of restriction sites of restriction enzymes and the second target sequence $L_n$ is added to a left side of the multiple cloning site; the sequence of the multiple cloning site of the second donor vector B2 is represented by "a vector backbone—the forward restriction site of the restriction enzyme at the even number site—the reverse restriction site of the cloning restriction enzyme—arbitrary bases—the forward restriction site of the cloning restriction enzyme—the reverse restriction site of the restriction enzyme at the odd number site—arbitrary bases—the forward restriction site of the restriction enzyme at the odd number site—the reverse restriction site of the restriction enzyme at the even number site—the vector backbone"; the vector backbone of the second donor vector B2 is in the absence of any restriction site of the cloning restriction enzyme, and n represents an even number, such as 2, 4, 6, 8, and so on;

2) introducing the first target sequence $L_m$ to the first donor vector B1, the step comprising: amplifying the first target sequence $L_m$ by PCR while adding restriction sites of restriction enzymes to two ends of the target sequence respectively via PCR primers, so that sticky ends of the target sequence after cleavage are the same as sticky ends of the first donor vector B1 after being cleaved by the cloning restriction enzyme, and cloning the first target sequence $L_m$ into the first donor vector B1 to replace the sequence of "—the reverse restriction site of the cloning restriction enzyme—arbitrary bases—the forward restriction site of the cloning restriction enzyme—" on the first donor vector B1, to yield a vector B1-$L_m$; and introducing the second target sequence $L_n$ to the second donor vector B2 comprising: amplifying the second target sequence $L_n$ by PCR while adding restriction sites of restriction enzymes to two ends of the target sequence respectively via PCR primers, so that sticky ends of the target sequence after cleavage are the same as sticky ends of the second donor vector B2 after being cleaved by the cloning restriction enzyme, and cloning the second target sequence $L_n$ into the second donor vector B2 to replace the sequence of "—the reverse restriction site of the cloning restriction enzyme—arbitrary bases—the forward restriction site of the cloning restriction enzyme—" on the second donor vector B2, to yield a vector B2-L$_n$, in which m represents an odd number, such as 1, 3, 5, 7, and so on, and n represents an even number, such as 2, 4, 6, 8, and so on; and 3) repeating 2) to assemble multiple fragments to yield a multi-fragment DNA molecule, the step comprising:

a) digesting the acceptor vector A1 and a vector B1-L$_1$ by a first restriction enzyme, and ligating the digested acceptor vector A1 and the digested vector B1-L$_1$ to transfer the target sequence L$_1$ from the vector B1-L$_1$ to the acceptor vector A1, to yield a vector A1-L$_1$;

b) digesting the vector A1-L$_1$ and a vector B2-L$_2$ by a second restriction enzyme, and ligating the vector A1-L$_1$ with the target sequence L$_2$ by a ligase, to yield a vector A1-L$_1$-L$_2$;

c) digesting the vector A1-L$_1$-L$_2$ and a vector B1-L$_3$ by a third restriction enzyme, and ligating the vector A1-L$_1$-L$_2$ with the target sequence L$_3$ by the ligase, to yield a vector A1-L$_1$-L$_2$-L$_3$; and d) continuing ligating the newly formed vector with another target sequence until a vector A1-L$_1$-L$_2$-L$_3$-L$_4$-L$_5$ . . . -L$_m$-L$_n$ is assembled, in which m represents an odd number, such as 1, 3, 5, 7, and so on, and n represents an even number, such as 2, 4, 6, 8, and so on.

In a class of this embodiment, a resistance of the acceptor vector A1 is different from both a resistance of the first donor vector B1 and a resistance of the second donor vector B2. The resistance of the first donor vector B1 is the same as or different from the resistance of the second donor vector B2.

The restriction enzymes are those having the restriction site and the restriction site not coincident with each other. The restriction enzyme features that the restriction site and the restriction site are not coincident, so that arbitrary sticky ends are produced. For a given DNA sequence, arbitrary specific sticky ends are produced.

The restriction enzymes belong to a typeIIs restriction enzyme or an artificially synthetic zinc-finger nuclease. The typeIIs restriction enzyme is one or several selected from BsmBI, BsaI, SapI, and BbsI.

The vector system in 1) is a Bio-Walk system. The acceptor vector A1 is an acceptor vector pBWA, the first donor vector B1 is a donor vector pBWD(a), and the second donor vector B2 is a donor vector pBWD(b).

The ligase is a T4 DNA ligase.

A method for gene synthesis, or a method for cloning a DNA fragment, or a method for multiple gene vector, comprises applying the method of assembling a multi-fragment DNA molecule.

Advantages of the method of assembling a multi-fragment DNA molecule according to embodiments of the invention are summarized as follows: the method realizes seamless linkage of multiple DNA fragments to generate a long DNA fragment. The method not only largely decreases mutations that easily occur in the large DNA fragment synthesis but also largely shortens the synthesis time. In the aspect of the large DNA fragment cloning, the mutations easily occurring in one-time cloning of the large DNA fragment are prevented. Small fragments are first cloned and sequenced, the correct fragments are quickly assembled into large fragments and then successively ligated with the acceptor vector, thus realizing the accumulation of the fragments and generating the integral DNA fragment in a short time. In the aspect of construction of the multi-gene vector, multiple genes can be constructed on the same vector and the one-step transformation is realized.

BRIEF DESCRIPTION OF THE DRAWINGS

The invention is described hereinbelow with reference to the accompanying drawings, in which.

DETAILED DESCRIPTION OF THE EMBODIMENTS

For further illustrating the invention, experiments detailing a method of assembling multi-fragment DNA molecule and applications thereof are described below. It should be noted that the following examples are intended to describe and not to limit the invention.

EXAMPLE 1

Construct of Bio-Walk System

Figure 1:
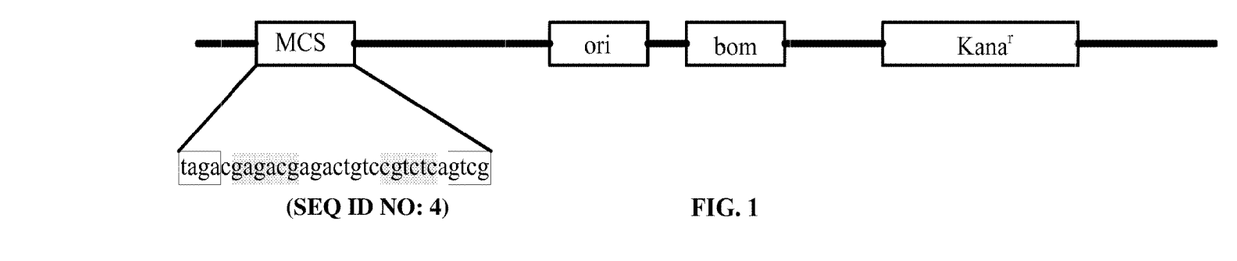
FIG. 1 illustrates a map and a multiple cloning site of pBWA in accordance with one embodiment of the invention.

1) An acceptor vector pBWA adopts a pBR322 replicon and has kanamycin resistance. The restriction enzyme at an odd number site (firstly accepted) is BsmBI. As shown in FIG. 1, a sequence of a multiple cloning site is SEQ ID NO: 4 represented by tagacgagacgagactgtccgtctcagtcg.

in which, gagacg and cgtctc are a reverse recognition sequence and a forward recognition sequence, respectively, and "taga" and "gtcg" are sticky ends produced by cleavage of BsmBI, respectively. MCS is a multiple cloning site, Kanar is Kanamycin resistance gene, ori is originated from a replication origin of the plasmid pBR322 and adapted to replicate in *Escherichia coli* cells, and bom is originated from a basis of mobility of the plasmid Pbr322.

Figure 2:
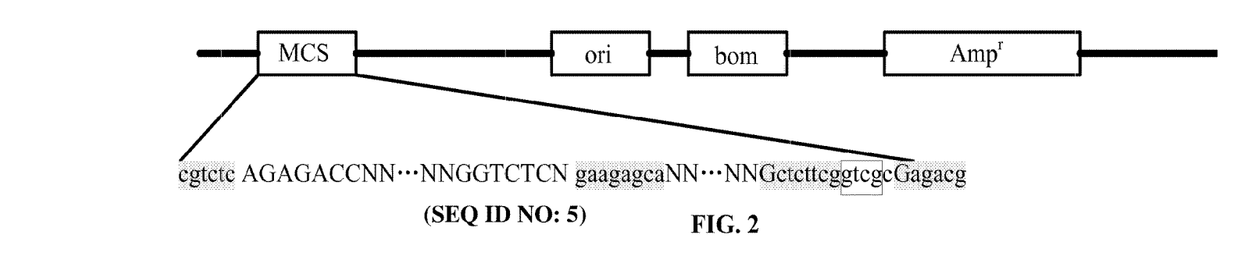
FIG. 2 illustrates a map and a multiple cloning site of pBWD(a) in accordance with one embodiment of the invention.

2) A first donor vector pBWD(a) contains an ampicillin resistance gene, and a map and a multiple cloning site thereof are illustrated in FIG. 2. A sequence of the multiple cloning site is SEQ ID NO: 5 represented by cgtctcAGAGACCNN . . . NNNGGTCTCN gaagagcaGctcttcgg tcgcGagacg In which, cgtctc and gagacg are the forward recognition sequence and the reverse recognition sequence of BsmbI, respectively. gagacc and ggtctc are a reverse recognition sequence and a forward recognition sequence of BsaI, respectively. gaagagc and gctcttc are a reverse recognition sequence and a forward recognition sequence of SapI, respectively. MCS is the multiple cloning site, Amp$^r$ represents the ampicillin resistance gene, ori is originated from the replication origin of the plasmid pBR322 and adapted to replicate in *Escherichia coli* cells, and bom is originated from the basis of mobility of the plasmid Pbr322. "N" represents arbitrary bases, and " ... " represents abbreviated arbitrary bases.

Figure 3:
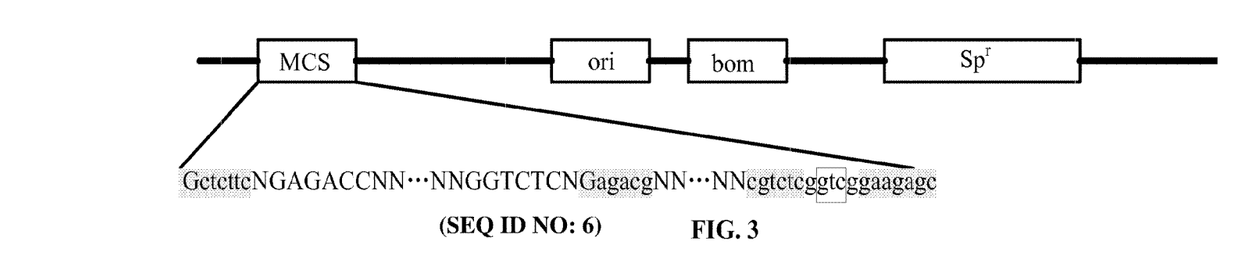
FIG. 3 illustrates a map and a multiple cloning site of pBWD(b) in accordance with one embodiment of the invention.

3) A second donor vector pBWD(b) contains a spectinomycin resistance gene, and a map and a multiple cloning site of the second donor vector pBWD(b) were illustrated in FIG. 3. A sequence of the multiple cloning site is SEQ ID NO: 6 represented by

```
GctcttcNGAGACCNN . . . NNGGTCTCNGagacgNNN . . . NNN
cgtctcggtcggaagagc.
``` in which, cgtctc and gagacg are the forward recognition sequence and the reverse recognition sequence of BsmbI, respectively. gagacc and ggtctc are the reverse recognition sequence and the forward recognition sequence of BsaI, respectively. gaagagc and gctcttc are the reverse recognition sequence and the forward recognition sequence of SapI, respectively. MCS represents the multiple cloning site, and Sp$^r$ represents the spectinomycin resistance gene. ori is originated from the replication origin of the plasmid pBR322 and adapted to replicate in *Escherichia coli* cells. bom is originated from the basis of mobility of the plasmid Pbr322. "N" represents arbitrary bases, and " ... " represents abbreviated arbitrary bases.

EXAMPLE 2

Multi-DNA Assembly by Bio-Walk System

First step, a target gene is cloned into the first donor vector pBWD(a). Five genes are adopted in this example.

pBWD(a)-GENE1

GENE1 is amplified using a forward primer "Gene1+" and a reverse primer "Gene1−" of GENE1. "catggagtcaaagattcaaatag" and "agcggatggcctaaaaaaaaac" are sequences of the forward primer and the reverse primer of GENE1, respectively. Full sequences of the Gene1+ and Gene1− are as follows:

```
Gene1 + (SEQ ID NO: 2):
ggtctcAtctcatagacatggagtcaaagattcaaatag

Gene1 - (SEQ ID NO: 3):
ggtctc t cttc tctagttttttttttaggccatccgct
```

A new sequence obtained from gene amplification by the above primers is as follows:

```
ggtctcAtctcataga-GENE1-tagagaagagacc
```

The MCS sequence of pBWD(a) is as follows:

```
cgtctc AGAGACCNN...NNGGTCTCNgaagagcaNN...NNGctcttggtcgcGagacg
```

The amplified new sequence and the MCS sequence are cleaved by BsaI (restriction sites of restriction enzymes are underscored) and sticky ends thereof after the cleavage are completely complementary at sites indicated by boxes. The PCR product of GENE1 after digested by the BsaI and the vector backbone digested by the BsaI are connected by a T4 DNA ligase to generate pBWD(a)-GENE1, a sequence structure of which is as follows:

```
pBWD(a)backbone--cgtctcAtaga-GENE1-tagagaagagcaNN...NNGctcttcggtcgcGagacg--pBWD(a)backbone
``` pBWD(a)-GENE3 and pBWD(a)-GENE5 are also generated by the same way, and sequence structures thereof are as follows:

pBWD(a)-GENE3:

```
pBWD(a)backbone--cgtctcAtaga-GENE3-tagagaagagcaNN...NNGctcttcggtcgcGagacg--pBWD(a)backbone
``` pBWD(a)-GENE5:

```
pBWD(a)backbone--cgtctcAtaga-GENE5-tagagaagagcaNN...NNGctcttcggtcgcGagacg--pBWD(a)backbone
```

Similar to the GENE1, GENE3, GENE5, Gene2 and Gene4 are amplified by adding different primer joints during amplification of the target genes (the forward primer joint is cgtctc A cttc a taga, and the reverse primer joint is cgtctc t tctc t tcta), the amplified gene (Gene2 or Gene4) and the second donor vector pBWD(b) are then cleaved by BsaI, and the sticky ends of the amplified gene and the second donor vector are completely complementary at sites indicated by boxes and then lignated by the T4 DNA ligase to generate pBWD(b)-GENE2 or pBWD(b)-GENE4. The sequence structure of pBWD(b)-GENE2 and pBWD(b)-GENE4 are listed as follows:

pBWD(b)-GENE2:

pBWD(b)backbone--Gctcttcataga-GENE2-tagaaGagacgNN...NNcgtctcggtcggaag age--pBWD(b)backbone pBWD(b)-GENE4:

pBWD(b)backbone--Gctcttcataga-GENE4-tagaaGagacgNN...NNcgtctcggtcggaa gage--pBWD(b)backbone Second step: target genes on pBWD(a)-GENE1, pBWD(a)-GENE3, pBWD(a)-GENE5 and the second donor vector pBWD(b) are assembled to the acceptor vector pBWA.

1. Construct of pBWA-1:
The sequence of the multiple cloning site of the acceptor vector pBWA is as follows:

pBWA-MCS:---tc taga cgagacgagactgtccgtctca gtcga----

The pBWA and the pBWD(a)-GENE1 are digested by BsmbI, and sticky ends thereof after the cleavage are completely complementary at sites indicated by boxes. Since the produced sticky ends are completely complementary, the backbone of the acceptor vector pBWA and the fragment of GENE1 are then ligated together by the T4 DNA ligase, and a newly produced sequence is named pBWA-1.

pBWA-1: -tc taga-GENE1-tagagaagagcaNN...NNGctcttcg gtcga---

2. Construct of pBWA-2:
The pBWA-1 and the pBWD(b)-GENE2 are digested by SapI, and sticky ends thereof after the cleavage are completely complementary at sites indicated by boxes. Since the produced sticky ends are completely complementary, the backbone of the acceptor vector pBWA-1 and the fragment of GENE2 are then ligated together by the T4 DNA ligase, and a newly produced sequence is named pBWA-2.

pBWA-2: -tctaga-GENE1-taga-GENE2-tagaaGagacgNN...NN cgtctcggtcga---

3. Construct of pBWA-3:

The pBWA-2 and the pBWD(a)-GENE3 are digested by BsmBI, since produced sticky ends are completely complementary, the backbone of the acceptor vector pBWA-2 and the fragment of GENE3 are then ligated by the T4 DNA ligase, and a newly produced sequence is named pBWA-3.

pBWA-3: -tctaga-GENE1-taga-GENE2-taga-GENE3-tagagaagagcaNN...NNGctcttcggtcga---

4. Construct of pBWA-4

The pBWA-3 and the pBWD(b)-GENE4 are digested by SapI, since produced sticky ends are completely complementary, the backbone of the acceptor vector pBWA-3 and the fragment of GENE4 are then ligated by the T4 DNA ligase, and a newly produced sequence is named pBWA-4.

pBWA-4:

-tctaga-GENE1-taga-GENE2-taga-GENE3-taga-GENE4-tagaaGagacgNN...NN cgtctcggtcga-

5. Construct of pBWA-5

The pBWA-4 and the pBWD(a)-GENE5 are digested by BsmbI, and sticky ends thereof after the cleavage are completely complementary at sites indicated by boxes. Since the produced sticky ends are completely complementary, the backbone of the acceptor vector pBWA-4 and the fragment of GENE5 are then ligated by the T4 DNA ligase, and a newly produced sequence is named pBWA-5.

pBWA-5:

-tctaga-GENE1-taga-GENE2-taga-GENE3-taga-GENE4-taga-GENE5-tagagaagagcaNN...NNGctcttcggtcga--

The operations are repeated likewise so as to assemble five or more genes to the acceptor vector.

EXAMPLE 3

Gene Synthesis and Cloning of Large DNA Fragment

Gene synthesis of Cos9. Gene Cos9 is an important mediated gene in the recently invented DNAi and originated from prokaryotes. Thus, the codon optimization is required in eukaryotes so as to realize a relative good expression of the Cos9, and the gene synthesis is necessitated. A total length of the sequence of Cos9 is 4147 bp, and a synthetic sequence (SEQ ID NO: 1) is as follows:

```
CCTAGGCCACCATGGACAAGAAGTACTCCATTGGGCTCGATATCG
GCACAAACAGCGTCGGCTGGGCCGTCATTACGGACGAGTACAAGG
TGCCGAGCAAAAAATTCAAAGTTCTGGGCAATACCGATCGCCACA
GCATAAAGAAGAACCTCATTGGCGCCCTCCTGTTCGACTCCGGGG
AAACGGCCGAAGCCACGCGGCTCAAAAGAACAGCACGGCGCAGAT
ATACCCGCAGAAGAATCGGATCTGCTACCTCCAGGAGATCTTTAG
TAATGAGATGGCTAAGGTGGATGACTCTTTCTTCCATAGGCTGGA
GGAGTCCTTTTTGGTGGAGGAGGATAAAAAGCACGAGCGCCACCC
AATCTTTGGCAATATCGTGGACGAGGTGGCGTACCATGAAAAGTA
CCCAACCATATATCATCTGAGGAAGAAGCTGGTAGACAGTACTGA
TAAGGCTGACTTGCGGTTGATCTATCTCGCGCTGGCGCACATGAT
CAAATTTCGGGGACACTTCCTCATCGAGGGGGACCTGAACCCAGA
CAACAGCGATGTGGACAAACTCTTTATCCAACTGGTTCAGACTTA
CAATCAGCTTTTCGAAGAGAACCCGATCAACGCATCCGGAGTTGA
CGCCAAAGCAATCCTGAGCGCTAGGCTGTCCAAATCCCGGCGGCT
CGAAAACCTCATCGCACAGCTCCCTGGGGAGAAGAAGAACGGCCT
GTTTGGTAATCTTATCGCCCTGTCACTCGGGCTGACCCCCAACTT
TAAATCTAACTTCGACCTGGCCGAAGATGCCAAGCTGCAACTGAG
CAAAGACACCTACGATGATGATCTCGACAATCTGCTGGCCCAGAT
CGGCGACCAGTACGCAGACCTTTTTTGGCGGCAAAGAACCTGTC
AGACGCCATTCTGCTGAGTGATATTCTGCGAGTGAACACGGAGAT
CACCAAAGCTCCGCTGAGCGCTAGTATGATCAAGCGCTATGATGA
GCACCACCAAGACTTGACTTTGCTGAAGGCCCTTGTCAGACAGCA
ACTGCCTGAGAAGTACAAGGAAATTTTCTTCGATCAGTCTAAAAA
TGGCTACGCCGGATACATTGACGGCGGAGCAAGCCAGGAGGAATT
```

-continued
```
TTACAAATTTATTAAGCCCATCTTGGAAAAAATGGACGGCACCGA
GGAGCTGCTGGTAAAGCTGAACAGAGAAGATCTGTTGCGCAAACA
GCGCACTTTCGACAATGGAAGCATCCCCCACCAGATTCACCTGGG
CGAACTGCACGCTATCCTCAGGCGGCAAGAGGATTTCTACCCCTT
TTTGAAAGATAACAGGGAAAAGATTGAGAAAATCCTCACATTTCG
GATACCCTACTATGTAGGCCCCCTCGCACGCGGAAATTCCAGATT
CGCGTGGATGACTCGCAAATCAGAAGAAACCATCACTCCCTGGAA
CTTCGAGGAAGTCGTGGATAAGGGGGCCTCTGCCCAGTCCTTCAT
CGAAAGGATGACTAACTTTGATAAAAATCTGCCTAACGAAAGGT
GCTTCCTAAACACTCTCTGCTGTACGAGTACTTCACAGTTTATAA
CGAACTCACCAAGGTCAAATACGTCACAGAAGGGATGAGAAAGCC
AGCATTCCTGTCTGGAGAGCAGAAGAAAGCTATCGTGGACCTCCT
CTTCAAGACGAACCGGAAAGTTACCGTGAAACAGCTCAAAGAGGA
CTATTTCAAAAAGATTGAATGTTTCGACTCTGTTGAAATCAGCGG
AGTGGAGGATCGCTTCAACGCATCCCTGGGAACGTATCACGATCT
CCTGAAAATCATTAAAGACAAGGACTTCCTGGACAATGAGGAGAA
CGAGGACATTCTTGAGGACATTGTCCTCACCCTTACGTTGTTTGA
AGATAGGGAGATGATTGAAGAACGCTTGAAAACTTACGCTCATCT
CTTCGACGACAAAGTCATGAAACAGCTCAAGAGGCGCCGATATAC
AGGATGGGGCGGCTGTCAAGAAAACTGATCAATGGGATTCGAGA
CAAGCAGAGTGGAAAGACAATCCTGGATTTTCTTAAGTCCGATGG
ATTTGCCAACCGGAACTTCATGCAGTTGATCCATGATGACTCTCT
CACCTTTAAGGAGGACATCCAGAAAGCACAAGTTTCTGGCCAGGG
GGACAGTCTGCACGAGCACATCGCTAATCTTGCAGGTAGCCCAGC
TATCAAAAAGGGAATACTGCAGACCGTTAAGGTCGTGGATGAACT
CGTCAAAGTAATGGGAAGGCATAAGCCCGAGAATATCGTTATCGA
GATGGCCCGAGAGAACCAAACTACCCAGAAGGGACAGAAGAACAG
TAGGGAAAGGATGAAGAGGATTGAAGAGGGTATAAAAGAACTGGG
GTCCCAAATCCTTAAGGAACACCCAGTTGAAAACACCCAGCTTCA
GAATGAGAAGCTCTACCTGTACTACCTGCAGAACGGCAGGGACAT
GTACGTGGATCAGGAACTGGACATCAATCGGCTCTCCGACTACGA
CGTGGATCATATCGTGCCCCAGTCTTTTCTCAAAGATGATTCTAT
TGATAATAAAGTGTTGACAAGATCCGATAAAAATAGAGGGAAGAG
TGATAACGTCCCCTCAGAAGAAGTTGTCAAGAAAATGAAAAATTA
TTGGCGGCAGCTGCTGAACGCCAAACTGATCACACAACGGAAGTT
CGATAATCTGACTAAGGCTGAACGAGGTGGCCTGTCTGAGTTGGA
TAAAGCCGGCTTCATCAAAAGGCAGCTTGTTGAGACACGCCAGAT
CACCAAGCACGTGGCCCAAATTCTCGATTCACGCATGAACACCAA
GTACGATGAAAATGACAAACTGATTCGAGAGGTGAAAGTTATTAC
TCTGAAGTCTAAGCTGGTGTCAGATTTCAGAAAGGACTTTCAGTT
```

-continued
```
TTATAAGGTGAGAGAGATCAACAATTACCACCATGCGCATGATGC
CTACCTGACCACCATGCGCATGATGCCTACCTGAATGCAGTGGTA
GGCACTGCACTTATCAAAAAATATCCCAAGCTGGAATCTGAATTT
GTTTACGGAGACTATAAAGTGTACGATGTTAGGAAAATGATCGCA
AAGTCTGAGCAGGAAATAGGCAAGGCCACCGCTAAGTACTTCTTT
TACAGCAATATTATGAATTTTTTCAAGACCGAGATTACACTGGCC
AATGGAGAGATTCGGAAGCGACCACTTATCGAAACAAACGGAGAA
ACAGGAGAAATCGTGTGGGACAAGGGTAGGGATTTCGCGACAGTC
CGGAAGGTCCTGTCCATGCCGCAGGTGAACATCGTTAAAAAGACC
GAAGTACAGACCGGAGGCTTCTCCAAGGAAAGTATCCTCCCGAAA
AGGAACAGCGACAAGCTGATCGCACGCAAAAAAGATTGGGACCCC
AAGAAATACGGCGGATTCGATTCTCCTACAGTCGCTTACAGTGTA
CTGGTTGTGGCCAAAGTGGAGAAAGGGAAGTCTAAAAAACTCAAA
AGCGTCAAGGAACTGCTGGGCATCACAATCATGGAGCGATCAAGT
TTCGAAAAAAACCCCATCGACTTTCTGGAGGCGAAAGGATATAAA
GAGGTCAAAAAAGACCTCATCATTAAGCTGCCCAAGTACTCTCTC
TTTGAGCTTGAAAACGGCCGGAAACGAATGCTCGCTAGTGCGGGC
GAGCTGCAGAAAGGTAACGAGCTGGCACTGCCCTCTAAATACGTT
AATTTCTTGTATCTGGCCAGCCACTATGAAAAGCTCAAAGGGTCC
CCCGAAGATAATGAGCAGAAGCAGCTGTTCGTGGAACAACACAAA
CACTACCTTGATGAGATCATCGAGCAAATAAGCGAGTTCTCCAAA
AGAGTGATCCTCGCCGACGCTAACCTCGATAAGGTGCTTTCTGCT
TACAATAAGCACAGGGATAAGCCCATCAGGGAGCAGGCAGAAAAC
ATTATCCACTTGTTTACTCTGACCAACTTGGGCGCACCTGCAGCC
TTCAAGTACTTCGACACCACCATAGACAGAAAGCGGTACACCTCT
ACAAAGGAGGTCCTGGACGCCACACTGATTCATCAGTCAATTACG
GGGCTCTATGAAACAAGAATCGACCTCTCTCAGCTCGGTGGAGAC
AGCAGGGCTGACCCCAAGAAGAAGAGGAAGGTG
```

The synthesis strategy is as follows: Cos9 is synthesized by dividing the gene into six fragments (the divided position is indicated by boxes in the above sequence), and each fragment containing between 600 and 700 bp. Each fragment is synthesized by asymmetric PCR method because the asymmetric PCR can only synthesize a DNA sequence containing less than 1000 bp. The six synthetic fragments are then cloned to pBWD(a) and pBWD(b) and are named as follows: pBWD(a)-cos91, pBWD(a)-cos93, pBWD(a)-cos95, pBWD(b)-cos92, pBWD(b)-cos94, pBWD(b)-cos96.

The synthesis process is as follows:

First step: the six fragments synthesized by the asymmetric PCR are cloned into the first donor vector pBWD(a) and the second donor vector pBWD(b) and are correctly sequenced. Sticky ends after cleavage are completely complementary at positions indicated by the boxes.

Structures of the vectors after cloning are as follows:

pBWD(a)-cos91:

pBWD(a)backbone-cgtctcAtagaCCTA-cos91-CTGGgaagagcaNN...NNGctcttcggtcgcGagacg-pBWD(a)backbone pBWD(b)-cos92:

pBWD(b)backbone-GctcttcaCTGG-cos92-CCTGaGagacgNN...NNcgtctcggtcggaagagc-pBWD(b)backbone pBWD(a)-cos93:

pBWD(a)backbone-cgtctcACCTG-cos93-ACTGgaagagcaNN...NNGctcttcggtcgcGagacg-pBWD(a)backbone pBWD(b)-cos94:

pBWD(b)backbone-GctcttcaACTG-cos94-GAGAaGagacgNN...NNcgtctcggtcggaagagc-pBWD(b)backbone pBWD(a)-cos95:

pBWD(a)backbone-cgtctcAGAGA-cos95-ATCAgaagagcaNN...NNGctcttcggtcgcGagacg-pBWD(a)backbone pBWD(b)-cos96:

pBWD(b)backbone-GctcttcaATCA-cos96-GGTGaGagacgNN...NNcgtctcggtcggaagagc-pBWD(b)backbone Second step: assembly of the DNA fragments. The sticky ends after the cleavage are completely complementary at positions indicated by boxes.

The multiple cloning site of the pBWA is as follows:

pBWA-MCS: ---tctagacgagacgagactgtccgtctcagtcga----

1. Construct of pBWA-cos9(1):

pBWA and pBWD(a)-cos91 are digested by BsmbI. Because produced sticky ends are completely complementary, the backbone of pBWA and the fragment cos91 are then ligated together by the T4 DNA ligase to generate pBWA-cos9(1).

pBWA-cos9(1): -tctagaccta-cos91-ctgggaagagcaNN...NNGctcttcggtcga---

2. Construct of pBWA-cos9(2):

pBWA-cos9(1) and pBWD(b)-cos92 are digested by SapI. Because produced sticky ends are completely complementary, the backbone of pBWA-cos9(1) and the fragment cos92 are then ligated together by the T4 DNA ligase to generate pBWA-cos9(2).

pBWA-cos9(2): -tctaga-cos91-ctgg-cos92-CCTGaGagacgNN…NNcgtctcggtcga-

3. Construct of pBWA-cos9(3):

pBWA-cos9(2) and pBWD(a)-cos93 are digested by BsmbI. Because produced sticky ends are completely complementary, the backbone of pBWA-cos9(2) and the fragment cos93 are then ligated together by the T4 DNA ligase to produce pBWA-cos9(3).

pBWA-cos9(3):

-tctaga-cos91-ctgg-cos92-CCTG-cos93-ACTGgaagagcaNN…NNGctcttcggtcga-

4. Construct of pBWA-cos9(4):

pBWA-cos9(3) and pBWD(b)-cos94 are digested by SapI. Because produced sticky ends are completely complementary, the backbone of pBWA-cos9(3) and the fragment cos94 are then ligated together by the T4 DNA ligase to form pBWA-cos9(4).

pBWA-cos9(4):

-tctaga-cos91-ctgg-cos92-CCTG-cos93-ACTG-cos94-GAGAaGagacgNN…NNcgtctcggtcga- 5. Construct of pBWA-cos9(5):

pBWA-cos9(4) and pBWD(a)-cos95 are digested by BsmbI. Because produced sticky ends are completely complementary, the backbone of pBWA-cos9(4) and the fragment cos95 are then ligated together by the T4 DNA ligase to form pBWA-cos9(5).

pBWA-cos9(5):

-tctaga-cos91-ctgg-cos92-CCTG-cos93-ACTG-cos94-GAGA-cos95-ATCAgaagagcaNN…NNGctcttcggtcga- 6. Construct of pBWA-cos9(6):

pBWA-cos9(5) and pBWD(b)-cos96 are digested by SapI. Because produced sticky ends are completely complementary, the backbone of pBWA-cos9(5) and the fragment cos96 are then ligated together by the T4 DNA ligase to form pBWA-cos9(6).

pBWA-cos9(6):

-tctaga-cos91-ctgg-cos92-CCTG-cos93-ACTG-cos94-GAGA-cos95-ATCA-cos96-GGTGaGagacgNN…NNcgtctcggtcga- Thus, the six fragments are seamlessly linked into an integral DNA fragment.

The long fragment DNA can be cloned by the method similarly to the long sequence synthesis method. The long sequence is firstly divided into small sequences which are then cloned and sequenced and finally seamlessly assembled into the long sequence by the Bio-Walk system.

Unless otherwise indicated, the numerical ranges involved in the invention include the end values. While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A method of assembling a multi-fragment DNA molecule, the method comprising:

1) providing an acceptor vector A1, a first donor vector B1, a second donor vector B2, a first restriction enzyme, a second restriction enzyme, and a third restriction enzyme; wherein the acceptor vector A1 comprises a first multiple cloning site; the first multiple cloning site comprises a reverse recognition site for the first restriction enzyme, a first sequence of random bases, and a forward recognition site for the first restriction enzyme; the reverse recognition site for the first restriction enzyme, the first sequence of random bases, and the forward recognition site for the first restriction enzyme are connected in sequence;

the first donor vector B1 comprises a second multiple cloning site; the second multiple cloning site comprises the forward recognition site for the first restriction enzyme, a reverse recognition site for the second restriction enzyme, a second sequence of random bases, a forward recognition site for the second restriction enzyme, a reverse recognition site for the third restriction enzyme, a third sequence of random bases, a forward recognition site for the third restriction enzyme, and the reverse recognition site for the first restriction enzyme; the forward recognition site for the first restriction enzyme, the reverse recognition site for the second restriction enzyme, the second sequence of random bases, the forward recognition site for the second restriction enzyme, the reverse recognition site for the third restriction enzyme, the third sequence of random bases, the forward recognition site for the third restriction enzyme, and the reverse recognition site for the first restriction enzyme are connected in sequence; and the second donor vector B2 comprises a third multiple cloning site; the third multiple cloning site comprises the forward recognition site for the third restriction enzyme, the reverse recognition site for the second restriction enzyme, a fourth sequence of random bases, the forward recognition site for the second restriction enzyme, the reverse recognition site for the first restriction enzyme, a fifth sequence of random bases, the forward recognition site for the first restriction enzyme, and the reverse recognition site for the third restriction enzyme; the forward recognition site for the third restriction enzyme, the reverse recognition site for the second restriction enzyme, the fourth sequence of random bases, the forward recognition site for the second restriction enzyme, the reverse recognition site for the first restriction enzyme, the fifth sequence of random bases, the forward recognition site for the first restriction enzyme, and the reverse recognition site for the third restriction enzyme are connected in sequence;

2) introducing a first target sequence $L_1$ to the first donor vector B1, comprising: amplifying the first target sequence $L_1$ by PCR while adding restriction sites for the second restriction enzyme to two ends of the first target sequence $L_1$, respectively, via PCR primers; and cloning the first target sequence $L_1$ into the first donor vector B1 by using the second restriction enzyme to replace the reverse recognition site for the second restriction enzyme, the second sequence of random bases, and the forward recognition site for the second restriction enzyme in the first donor vector B1 with the first target sequence $L_1$ to yield a vector B1-$L_1$;

introducing a third target sequence $L_3$ to the first donor vector B1, comprising: amplifying the third target sequence $L_3$ by PCR while adding restriction sites for the second restriction enzyme to two ends of the third target sequence $L_3$, respectively, via PCR primers; and cloning the third target sequence $L_3$ into the first donor vector B1 by using the second restriction enzyme to replace the reverse recognition site for the second restriction enzyme, the second sequence of random bases, and the forward recognition site for the second restriction enzyme in the first donor vector B1 with the third target sequence $L_3$ to yield a vector B1-$L_3$;

introducing a fifth target sequence $L_5$ to the first donor vector B1 , comprising: amplifying the fifth target sequence $L_5$ by PCR while adding restriction sites for the second restriction enzyme to two ends of the fifth target sequence $L_5$, respectively, via PCR primers; and cloning the fifth target sequence $L_5$ into the first donor vector B1 by using the second restriction enzyme to replace the reverse recognition site for the second restriction enzyme, the second sequence of random bases, and the forward recognition site for the second restriction enzyme in the first donor vector B1 with the fifth target sequence $L_5$ to yield a vector B1-$L_5$;

introducing a second target sequence $L_2$ to the second donor vector B2, comprising: amplifying the second target sequence $L_2$ by PCR while adding restriction sites for the second restriction enzyme to two ends of the second target sequence $L_2$, respectively, via PCR primers; and cloning the second target sequence $L_2$ into the second donor vector B2 by using the second restriction enzyme to replace the reverse recognition site for the second restriction enzyme, the fourth sequence of random bases, and the forward recognition site for the second restriction enzyme in the second donor vector B2 with the second target sequence $L_2$ to yield a vector B2-$L_2$;

introducing a fourth target sequence $L_4$ to the second donor vector B2, comprising: amplifying the fourth target sequence $L_4$ by PCR while adding restriction sites for the second restriction enzyme to two ends of the fourth target sequence $L_4$ , respectively, via PCR primers; and cloning the fourth target sequence $L_4$ into the second donor vector B2 by using the second restriction enzyme to replace the reverse recognition site for the second restriction enzyme, the fourth sequence of random bases, and the forward recognition site for the second restriction enzyme in the second donor vector B2 with the fourth target sequence $L_4$ to yield a vector $B2-L_4$; and introducing a sixth target sequence $L_6$ to the second donor vector B2, comprising: amplifying the sixth target sequence $L_6$ by PCR while adding restriction sites for the second restriction enzyme to two ends of the sixth target sequence $L_6$, respectively, via PCR primers; and cloning the sixth target sequence $L_6$ into the second donor vector B2 by using the second restriction enzyme to replace the reverse recognition site for the second restriction enzyme, the fourth sequence of random bases, and the forward recognition site for the second restriction enzyme in the second donor vector B2 with the sixth target sequence $L_6$ to yield a vector $B2-L_6$; and 3) digesting the acceptor vector A1 and the vector $B1-L_1$ by the first restriction enzyme to obtain a digested acceptor vector A1 and a digested $L_1$ sequence, respectively, and ligating the digested acceptor vector A1 and the digested $L_1$ sequence using a ligase to yield a vector $A1-L_1$;

digesting the vector $A1-L_1$ and the vector $B2-L_2$ by the third restriction enzyme to obtain a digested vector $A1-L_1$ and a digested $L_2$ sequence, respectively, and ligating the digested vector $A1-L_i$ and the digested $L_2$ sequence using the ligase to yield a vector $A1-L_1-L_2$;

digesting the vector $A1-L_1-L_2$ and the vector $B1-L_3$ by the first restriction enzyme to obtain a digested vector $A1-L_1-L_2$ and a digested $L_3$ sequence, respectively, and ligating the digested vector $A1-L_1-L_2$ and the digested $L_3$ sequence using the ligase to yield a vector $A1-L_1-L_2-L_3$;

digesting the vector $A1-L_1-L_2-L_3$ and the vector $B2-L_4$ by the third restriction enzyme to obtain a digested vector $A1-L_1-L_2-L_3$ and a digested $L_4$ sequence, respectively, and ligating the digested vector $A1-L_1-L_2-L_3$ and the digested $L_4$ sequence using the ligase to yield a vector $A1-L_1-L_2-L_3-L_4$;

digesting the vector $A1-L_1-L_2-L_3-L_4$ and the vector $B1-L_5$ by the first restriction enzyme to obtain a digested vector $A1-L_1-L_2-L_3-L_4$ and a digested $L_5$ sequence, respectively, and ligating the digested vector $A1-L_1-L_2-L_3-L_4$ and the digested $L_5$ sequence using the ligase to yield a vector $A1-L_1-L_2-L_3-L_4-L_5$; and digesting the vector $A1-L_1-L_2-L_3-L_4-L_5$ and the vector $B2-L_6$ by the third restriction enzyme to obtain a digested vector $A1-L_1-L_2-L_3-L_4-L_5$ and a digested $L_6$ sequence, respectively, and ligating the digested vector $A1-L_1-L_2-L_3-L_4-L_5$ and the digested $L_6$ sequence using the ligase to yield a multi-fragment DNA molecule $A1-L_1-L_2-L_3-L_4-L_5-L_6$.

2. The method of claim 1, wherein
the acceptor vector A1 comprises a kanamycin resistance gene;
the first donor vector B1 comprises an ampicillin resistance gene; and
the second donor vector B2 comprises a spectinomycin resistance gene.

3. The method of claim 1, wherein the ligase is a T4 DNA ligase.

4. A method of gene synthesis, or cloning a DNA fragment, or constructing a multiple gene vector, comprising applying the method of assembling multi-fragment DNA molecule of claim 1.

5. The method of claim 1, wherein
the first restriction enzyme is BsmBI;
the second restriction enzyme is BsaI; and
the third restriction enzyme is SapI.

\* \* \* \* \*